(12) United States Patent
Bobbitt

(10) Patent No.: US 11,497,536 B2
(45) Date of Patent: Nov. 15, 2022

(54) SURGICAL INSTRUMENT AND METHOD

(71) Applicant: WARSAW ORTHOPEDIC INC., Warsaw, IN (US)

(72) Inventor: Dustin Bobbitt, Olive Branch, MS (US)

(73) Assignee: Warsaw Orthopedic, Inc., Warsaw, IN (US)

(*) Notice: Subject to any disclaimer, the term of this patent is extended or adjusted under 35 U.S.C. 154(b) by 58 days.

(21) Appl. No.: 17/064,974

(22) Filed: Oct. 7, 2020

(65) Prior Publication Data

US 2021/0022779 A1 Jan. 28, 2021

Related U.S. Application Data

(62) Division of application No. 15/938,358, filed on Mar. 28, 2018, now Pat. No. 10,828,072.

(51) Int. Cl.
*A61B 17/70* (2006.01)
(52) U.S. Cl.
CPC ........ *A61B 17/7086* (2013.01); *A61B 17/705* (2013.01); *A61B 17/7034* (2013.01)

(58) Field of Classification Search
None
See application file for complete search history.

(56) References Cited

U.S. PATENT DOCUMENTS

| 7,572,281 | B2* | 8/2009 | Runco | A61B 17/7086 |
| | | | | 606/279 |
| 2004/0176775 | A1* | 9/2004 | Burkus | A61B 90/94 |
| | | | | 606/90 |
| 2011/0028979 | A1* | 2/2011 | Schwab | A61B 17/3209 |
| | | | | 606/83 |
| 2018/0338783 | A1* | 11/2018 | Mire | A61B 17/7001 |

* cited by examiner

*Primary Examiner* — Tessa M Matthews
(74) *Attorney, Agent, or Firm* — Sorell, Lenna & Schmidt, LLP

(57) ABSTRACT

A surgical instrument includes a body member having a proximal portion and a distal portion. The distal portion includes a first surface defining a first implant cavity and a second surface defining a second implant cavity. The second surface is engageable with an implant and includes a pivot. In some embodiments, spinal constructs, implants, systems and methods are disclosed.

20 Claims, 5 Drawing Sheets

SURGICAL INSTRUMENT AND METHOD

CROSS-REFERENCE TO RELATED APPLICATION

This application is a divisional of U.S. patent application Ser. No. 15/938,358, filed Mar. 28, 2018, which is expressly incorporated herein by reference, in its entirety.

TECHNICAL FIELD

The present disclosure generally relates to medical devices for the treatment of spinal disorders, and more particularly to a surgical system and a method for correction of a spinal disorder.

BACKGROUND

Spinal disorders such as degenerative disc disease, disc herniation, osteoporosis, spondylolisthesis, stenosis, kyphosis, scoliosis and other curvature abnormalities, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, corpectomy, discectomy, lam inectomy, fusion, fixation and implantable prosthetics. As part of these surgical treatments, spinal constructs including vertebral rods are often used to provide stability to a treated region. Rods redirect stresses away from a damaged or defective region while healing takes place to restore proper alignment and generally support vertebral members. The rods may be attached via fasteners to an exterior of two or more vertebral members. In some cases, the spinal constructs may be manipulated with surgical instruments for positioning and alignment in connection with the surgical treatment. This disclosure describes an improvement over these prior technologies.

SUMMARY

In one embodiment, a surgical instrument is provided. The surgical instrument includes a body member having a proximal portion and a distal portion. The distal portion includes a first surface defining a first implant cavity and a second surface defining a second implant cavity. The second surface is engageable with an implant and includes a pivot. In some embodiments, spinal constructs, implants, systems and methods are disclosed.

In one embodiment, a method for treating spine is provided. The method includes the steps of: connecting a bone fastener with vertebral tissue, the bone fastener including a first receiver and a second receiver; disposing a first spinal rod with the first receiver; disposing a second spinal rod adjacent the second receiver; engaging a first surface of a surgical instrument with the first spinal rod and a second surface of the surgical instrument with the second spinal rod, the surgical instrument including a pivot; and rotating the surgical instrument about the pivot to dispose the second spinal rod in the second receiver.

In one embodiment, a spinal implant system is provided. The spinal implant system includes a bone fastener having a threaded shaft, a first receiver and a second receiver. The shaft is aligned with the second receiver. The system includes a first spinal rod, a second spinal rod and a surgical instrument. The surgical instrument includes a pivot, a first surface engageable with the first rod and a second surface engageable with the second rod. The surgical instrument is rotatable about the pivot to dispose the rods with the receivers.

BRIEF DESCRIPTION OF THE DRAWINGS

The present disclosure will become more readily apparent from the specific description accompanied by the following drawings, in which.

DETAILED DESCRIPTION

Figure 1:
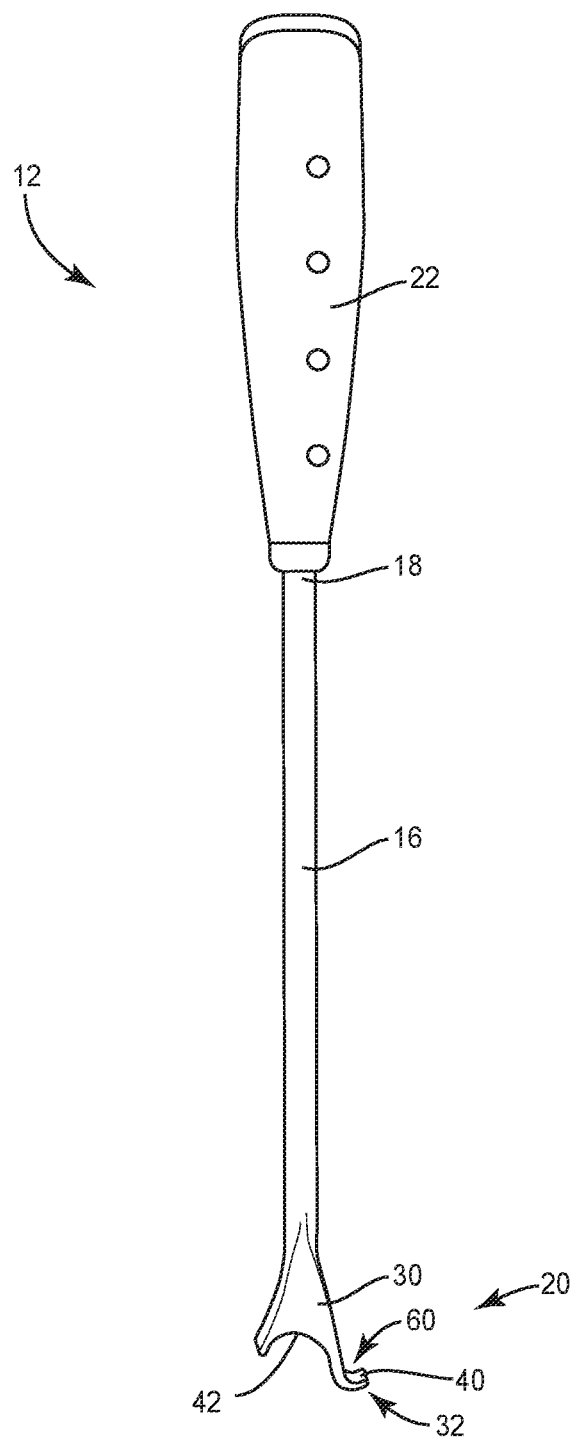
FIG. 1 is a first side view of components of one embodiment of a surgical system, including a handle and a body member having a proximal portion and a distal portion, in accordance with the principles of the present disclosure.
Figure 2:
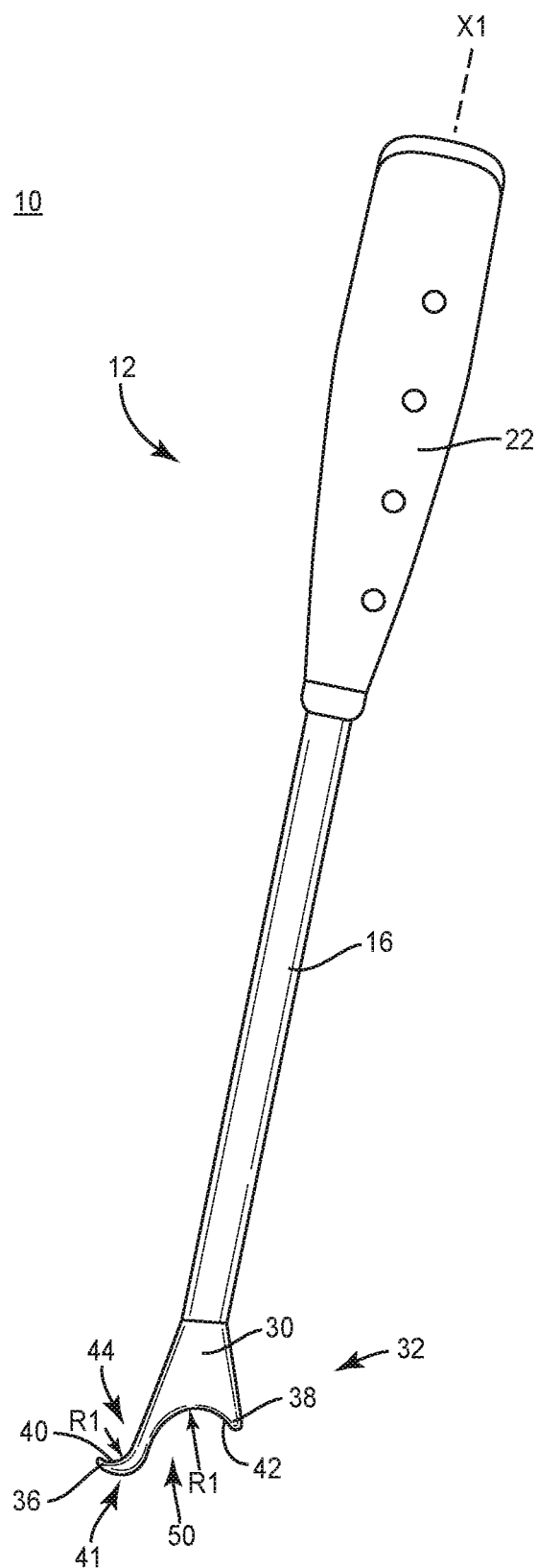
FIG. 2 is a second side view of components of one embodiment of a surgical system, including a body portion, in accordance with the principles of the present disclosure.

The exemplary embodiments of the system and related methods of use disclosed are discussed in terms of medical devices for the treatment of musculoskeletal disorders and more particularly, in terms of a surgical system and method for correction of a spine disorder. In some embodiments, the present surgical system comprises a surgical instrument that can be employed with one or more components of a spinal construct for surgical treatment of a spine including, for example, a pedicle subtraction osteotomy (PSO) or a three column osteotomy (3CO). In some embodiments, the present surgical system can be employed with a posterior vertebral column resection to correct angular and fixed kyphotic deformity, such as post traumatic deformity, congenital deformity and/or post infectious deformity.

In some embodiments, the present surgical system comprises a surgical instrument including an adjacent spinal rod reducer. In some embodiments, the surgical instrument reduces a spinal rod by prying and/or leveraging against a surface of one or more components of a spinal construct. In some embodiments, the surgical instrument is engageable with the surface for prying or leverage and movable in a medial lateral orientation of vertebrae of a spine. In some embodiments, the surgical instrument is rotatable in a medial lateral orientation of vertebrae of a spine for manipulating one or more components of a spinal construct. In some embodiments, this configuration of the surgical instrument avoids the drawbacks of manipulating spinal implants in tight or overcrowded workspaces and/or the difficulties associated with manipulating additional implants in such workspaces by providing medial-lateral rotation. For example, this configuration allows adding spinal rods for surgical treatment to strengthen a spinal construct.

In some embodiments, the present surgical system comprises a surgical instrument including a tip that hooks onto an existing spinal rod implant and/or existing implant component of a spinal construct to create a pivot point for applying leverage. In some embodiments, the surgical instrument includes a heel that receives a spinal rod or an implant component of a spinal construct. In some embodiments, the heel includes a configuration and/or geometry that directs a spinal rod and/or an implant component of a spinal construct into a selected position relative to a spinal rod, an implant component of a spinal construct and/or vertebral tissue as the heel pivots around the tip.

In some embodiments, the present surgical system is employed with a method that includes the steps of inserting bone screws in two vertebrae above and two vertebrae below a PSO site. In some embodiments, the present surgical system can include or be used with multi-axial screws (MAS) and/or dual rod multi-axial screws (DRMAS). In some embodiments, the present surgical system includes a surgical instrument that can compress or distract and restore curvature of a spine. In some embodiments, the present surgical system includes instruments and tools for correcting a sagittal deformity and rebalancing a spine of a body. In some embodiments, the present surgical system is employed to treat degenerative deformities of a spine in a sagittal plane, for example, ankylosing spondylitis. In some embodiments, the present surgical system is employed to treat hyper-kyphosis, flat lumbar back and cervical hyper lordosis, including disorders that create an unbalance of a body and loss of alignment between body parts. In some embodiments, the present surgical system provides a selected amount of correction to apply a selected balance to a spine and provides control and adjustment to the amount of correction. In some embodiments, the present surgical system includes a series of tools and instruments that allow formulation of a type of correction applied and can control the correction stabilization using posterior instrumentation.

In some embodiments, one or all of the components of the surgical system are disposable, peel-pack, pre-packed sterile devices used with an implant. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made to the exemplary embodiments of the present disclosure, which are illustrated in the accompanying figures. Turning to FIGS. 1-6, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals), ceramics and composites thereof such as calcium phosphate (e.g., SKEL-ITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of spinal implant system 10 are configured for engagement with spinal constructs attached with vertebrae to manipulate tissue and/or correct a spinal disorder, such as, for example, a sagittal deformity, as described herein. In some embodiments, spinal implant system 10 may be employed with surgical procedures, such as, for example, PSO, 3CO, corpectomy, discectomy and/or fracture/trauma treatment and may include fusion and/or fixation that employ implants to restore the mechanical support function of vertebrae. In some embodiments, one or more of the components of spinal implant system 10 are configured for engagement with existing constructs, which may include fastener implants and/or spinal rod implants attached with vertebrae, in a revision surgery to manipulate tissue and/or correct a spinal disorder, as described herein. In some embodiments, one or more of the components of spinal implant system 10 can be employed in a revision surgery to connect an existing spinal construct and extend, revise or repair the existing spinal construct to span one or more spinal levels. In some embodiments, one or more components of spinal implant system 10 are configured to extend an existing spinal rod implant with or without removing the existing rod implant. In some embodiments, existing spinal constructs may include one or more implants connected or fixed with tissue in a prior or different surgical procedure, separate in time and/or over a duration of time in the same surgical procedure.

Spinal implant system 10 includes a surgical instrument, such as, for example, a rod reducer 12. Reducer 12 is configured for engagement with spinal implants connectable with a dual-rod-holding bone fastener 110. Reducer 12 is utilized to reduce a spinal implant, for example, a spinal rod 204 with bone fastener 110 by employing leverage and/or mechanical advantage created by a pivot 60, as described herein, of reducer 12 due to engagement of reducer 12 with an adjacent spinal implant, for example, a spinal rod 200 that is fixed with bone fastener 110. In some embodiments, spinal rod 204 includes a resistance and/or load and the mechanical advantage and leverage is employed to facilitate reduction of spinal rod 204 with bone fastener 110, as described herein. In some embodiments, reducer 12 includes a lever configuration such that pivot 60 corresponds to and/or is aligned with a surface of reducer 12 that engages spinal rod 200 to provide a fulcrum of the lever configuration. In some embodiments, reducer 12 includes a lever configuration such that a surface configured for engagement with spinal rod 200 includes one or a plurality of pivot points and/or surfaces 60 as spinal rod 200 is caused to move along reducer 12 during reduction of spinal rod 204 with bone fastener 110, as described herein.

Reducer 12 includes a body member 16. Member 16 extends between a proximal portion 18 and a distal portion 20 defining a longitudinal axis X1. Portion 18 includes a handle 22 configured to facilitate manipulation of reducer 12. Handle 22 extends along axis X1. Handle 22 may have any of various cross section configurations, such as, for example, oval, oblong, triangular, square, hexagonal, polygonal, irregular, uniform, non-uniform and/or tapered. In some embodiments, handle 22 may be disposed at alternate orientations relative to member 16, such as, for example, transverse, perpendicular and/or other angular orientations such as acute or obtuse.

Distal portion 20 includes a body 30 and a distal end 32. In some embodiments, distal end 32 includes a distal tip. Body 30 extends in a tapered configuration having an increasing width from body member 16 to distal end 32. In some embodiments, body 30 includes a decreasing width between body member 16 and distal end 32. In some embodiments, body 30 includes a uniform width between body member 16 and distal end 32. In some embodiments, body 30 may have various configurations, for example, round, oval, rectangular, polygonal, irregular, offset, staggered, uniform and non-uniform.

Distal end 32 includes a wall 34 that extends between an end 36 and an end 38. Wall 34 includes an undulating cross section between end 36 and end 38. Wall 34 includes a rod engaging portion, such as, for example, a surface 40 and a rod engaging portion, such as, for example, a surface 42. Surface 40 is oriented a distance from surface 42 to facilitate alignment with spaced apart receivers 118, 218 of bone fastener 110, as described herein.

Wall 24 includes an arm having surface 40 extending downward and away from body member 16 in a first direction. Surface 40 defines an implant cavity 44 configured for disposal and/or capture of a spinal implant, such as, for example, a spinal rod 200. Surface 40 includes an arcuate configuration having a radius of curvature R1. In some embodiments, surface 40 is configured as a hook 41. Surface 40 engages an outer surface 202 of spinal rod 200 to define pivot 60, as described herein, and provide a mechanical advantage and leverage for reduction of spinal rod 204 with receiver 218.

Surface 40 includes pivot 60, at which point, surface 60 contacts outer surface 202 of spinal rod 200. The pivot is not limited to be a point, per se, and may, for example, include an area or region interacting with outer surface 202 of rod 200 in operation of spinal implant system 10. Reducer 12 is pivotable about pivot 60 to apply leverage to the load and/or resistance of spinal rod 204 for reduction with bone fastener 110. In some embodiments, pivot 60 includes one or a plurality of points and/or surfaces of surface 40. In some embodiments, pivot 60 includes one or a plurality of pivot points and/or surfaces corresponding to and/or aligned with the portion of surface 40 engaging spinal rod 200. In some embodiments, all or only a portion of surface 40 includes pivot 60. In some embodiments, pivot 60 is disposed with wall 34 and not contacting spinal rod 200. In some embodiments, surface 40 is configured for slidable engagement with surface 202 during rotation of reducer 12. In some embodiments, all or only a portion of surface 40 may have alternate surface configurations to enhance engagement with spinal rod 200 such as, for example, rough, arcuate, undulating, mesh, porous, semi-porous, dimpled and/or textured.

Wall 24 includes an arm having surface 42 extending downward and away from body member 16 in a second direction. Surface 42 defines an implant cavity 50 configured for disposal and capture of spinal rod 204. Surface 42 includes an arcuate configuration having a radius of curvature R2. Curvature R2 is greater than curvature R1. In some embodiments, curvature R1 is equal to curvature R2. In some embodiments, curvature R1 is greater than curvature R2. Surface 42 is configured to rotate into engagement with spinal rod 204 such that surface 42 applies a force to spinal rod 204 to seat spinal rod 204 with receiver 218. In some embodiments, surface 42 is configured for slidable engagement with spinal rod 204 during rotation of reducer 12. In some embodiments, all or only a portion of surface 42 may have alternate surface configurations to enhance engagement with spinal rod 204 such as, for example, rough, arcuate, undulating, mesh, porous, semi-porous, dimpled and/or textured.

Bone fastener 110 includes a dual rod receiver configuration, such as, for example, a dual rod multi-axial screw (DRMAS) and/or a dual rod sagittal adjusting screw (DR-SAS). Bone fastener 110 includes a head 112 and a shaft 114. In some embodiments, head 112 is selectively movable relative to shaft 114 through an angular range and disposable at a selected angle relative to shaft 114. In some embodiments, head 112 is selectively movable relative to shaft 114 through an angular range of 0-180 degrees. In some embodiments, the selected movement of head 112 includes rotation and/or pivotal movement of head 112 relative to shaft 114 about one or a plurality of axes. In some embodiments, the selected movement of head 112 includes rotation and/or pivotal movement of head 112 relative to shaft 114 through one or a plurality of planes. In some embodiments, the selected movement includes movement through one or more of transverse, vertical, horizontal, diagonal, coronal and/or sagittal planes of a body. In some embodiments, head 112 is disposed in a fixed orientation relative to shaft 114.

Figure 3:
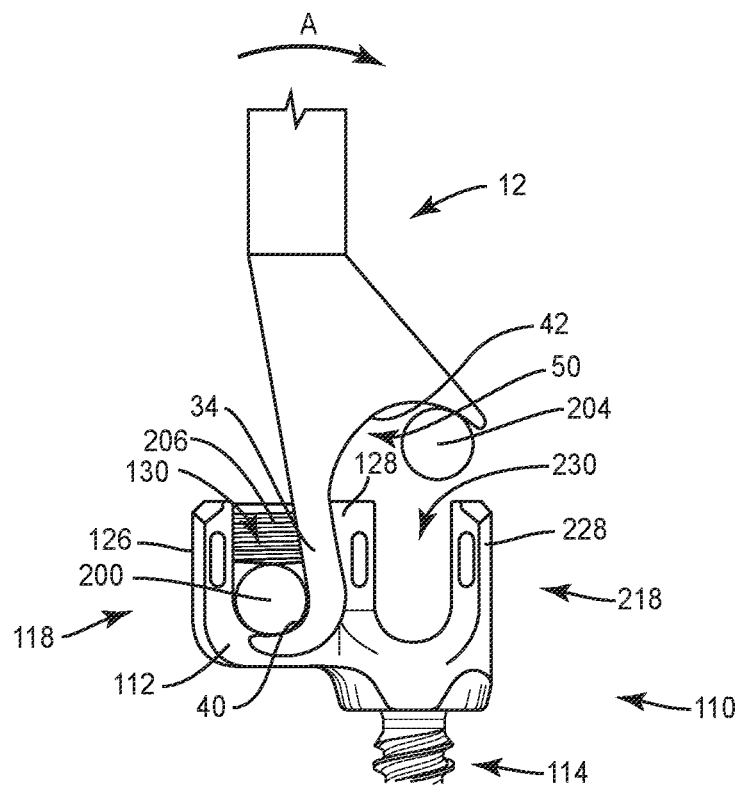
FIG. 3 is a break away side view of components of one embodiment of a surgical system, in a first use position, in accordance with the principles of the present disclosure.

Head 112 includes receiver 118. Receiver 118 includes an arm 126 and a portion of an intermediate arm 128. Arm 126 and the portion of arm 128 are spaced apart to define an implant cavity, such as, for example, a rod slot 130 therebetween. Rod slot 130 is configured for top loading of spinal rod 200, as shown in FIG. 3. In some embodiments, rod slot 130 is configured for side loading or has a closed configuration. Receiver 118 includes an inner surface that defines a thread form configured for engagement with a coupling member, such as, for example, a set screw 206, to retain spinal rod 200 within rod slot 130.

Head 112 includes receiver 218, similar to receiver 118, having an arm 228 and a portion of arm 128, which are spaced apart to define a rod slot 230 therebetween. Receiver 218 is aligned with shaft 114. Rod slot 230 is configured for top loading of spinal rod 204, as shown in FIG. 3. In some embodiments, receiver 218 may be disposed in various orientations, such as, for example, perpendicular, transverse and/or at angular orientations, such as acute or obtuse relative to receiver 118. In some embodiments, receiver 218 may be disposed offset or staggered relative to receiver 118, as described herein. Rod slot 230 is disposed separate and apart from rod slot 130. Receiver 218 includes an inner surface that defines a thread form configured for engagement with a coupling member, such as, for example, a set screw (not shown), to retain spinal rod 204 within rod slot 230.

In assembly, operation and use, spinal implant system 10 including reducer 12, similar to the systems and methods described herein, is employed with a surgical procedure, such as, for example, a correction treatment of an applicable condition or injury of an affected section of a spinal column and adjacent areas within a body. Spinal implant system 10 may be completely or partially revised, removed or replaced.

In some embodiments, spinal implant system 10 comprises a spinal construct that can be employed with one or more surgical instruments for various surgical procedures, such as, for example, PSO, 3CO or revision surgery to extend an existing screw and spinal rod construct. In some embodiments spinal implant system 10 can be employed with a posterior vertebral column resection to correct angular and fixed kyphotic deformity, such as post traumatic deformity, congenital deformity and/or post infectious deformity.

In use, to treat a selected section of vertebrae V, as shown in FIGS. 3-7, a medical practitioner obtains access to a surgical site including vertebrae V in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of vertebrae V, as well as for aspiration and irrigation of a surgical region.

Bone fasteners 110, as described herein, are engaged with vertebrae V along a lateral side L of vertebrae V. Each shaft 114 is manipulated to drive, torque, insert or otherwise connect a bone fastener 110 with vertebrae V. Spinal rod 200 is delivered along the surgical pathway to a surgical site adjacent vertebrae V. Spinal rod 200 is disposed with receiver 118 along vertebrae V. Spinal rod 200 is manipulated to dispose spinal rod 200 with rod slot 130 from a top loading orientation.

Figure 7:
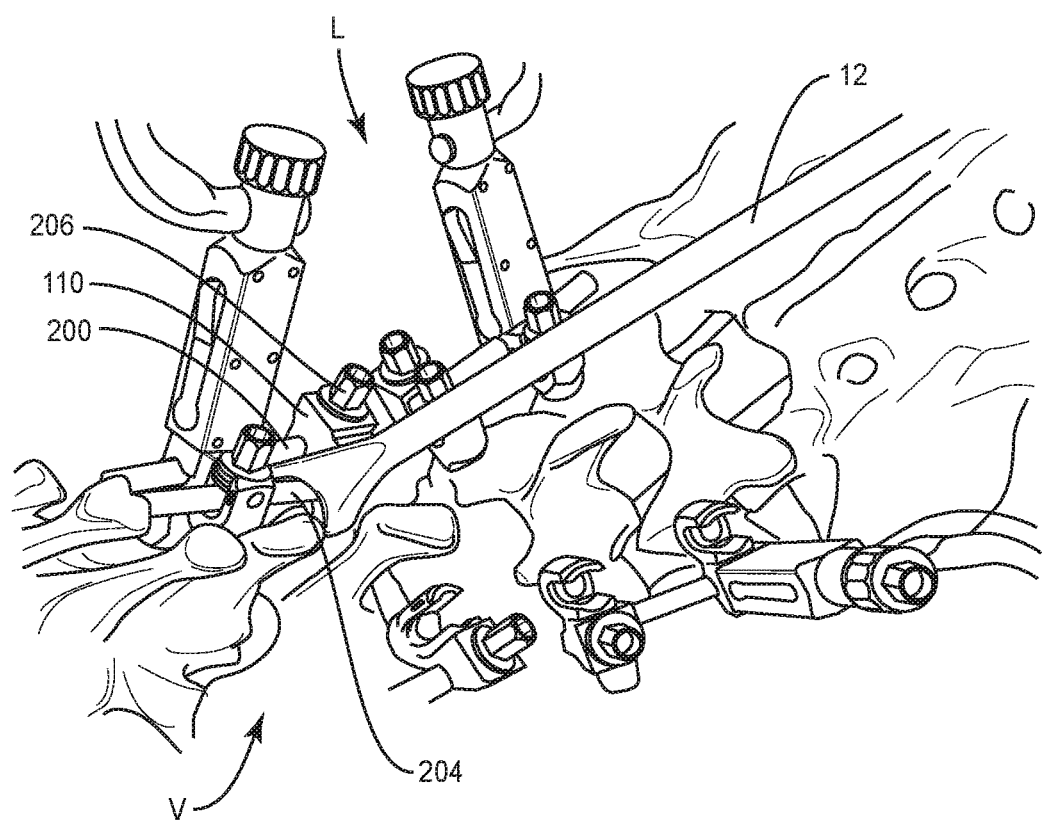
FIG. 7 is a perspective view of components of one embodiment of a surgical system, in use with a spinal implant construct, in accordance with the principles of the present disclosure disposed with vertebrae.

Spinal rod 200 is fixed with receiver 118 with a set screw 206, as shown in FIG. 7. Set screw 206 is engaged with a surgical instrument, such as, for example, a driver (not shown), which advances set screw 206 into engagement with receiver 118 in a locking orientation, as described herein. The driver engages set screw 206 to provisionally fix spinal rod 200 with receiver 118 and for attachment of spinal rod 200 with vertebrae V. In some embodiments, spinal rod 200 is permanently fixed with receiver 118.

Spinal rod 204 is oriented in a top loading position and disposed adjacent receiver 218 along vertebrae V, as shown in FIG. 7. Reducer 12 is disposed adjacent the surgical site and bone fastener 110. Reducer 12 is manipulated, via handle 22, to dispose distal end 32 with the surgical site and adjacent bone fastener 110 and spinal rods 200, 204. Surface 40 is oriented and aligned with spinal rod 200 to capture spinal rod 200 with cavity 44, as shown in FIG. 3. Surface 40 is engaged with surface 202 of spinal rod 200 to define pivot 60. A portion of surface 40 that engages surface 202 includes pivot 60, which comprises one or a plurality of points and/or surfaces 60a of surface 40. Engagement of surface 40 with spinal rod 200 creates pivot 60 to provide leverage and/or mechanical advantage, as described herein. In some embodiments, reducer 12 includes a lever configuration such that pivot 60 corresponds to and/or is aligned with engagement of surface 40 and spinal rod 200 to provide a fulcrum of the lever configuration.

Figure 4:
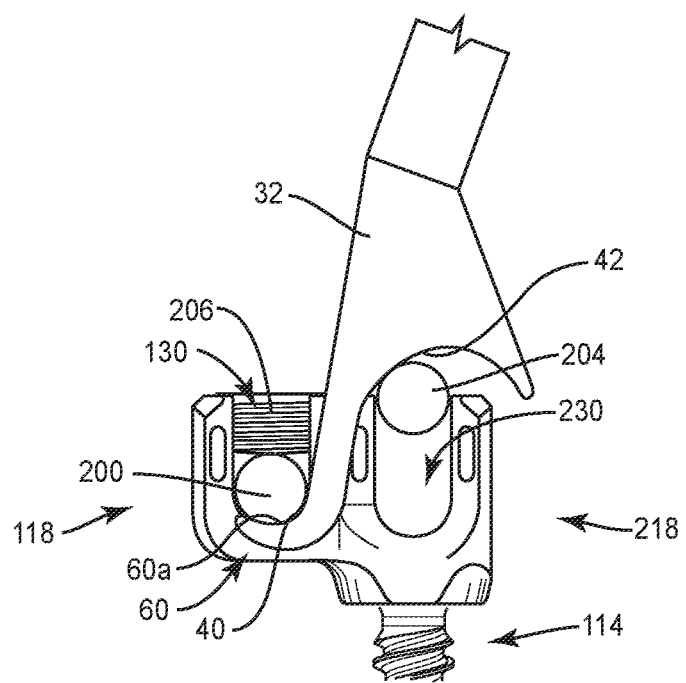
FIG. 4 is a break away side view of the components shown in FIG. 3, in a second use position.
Figure 5:
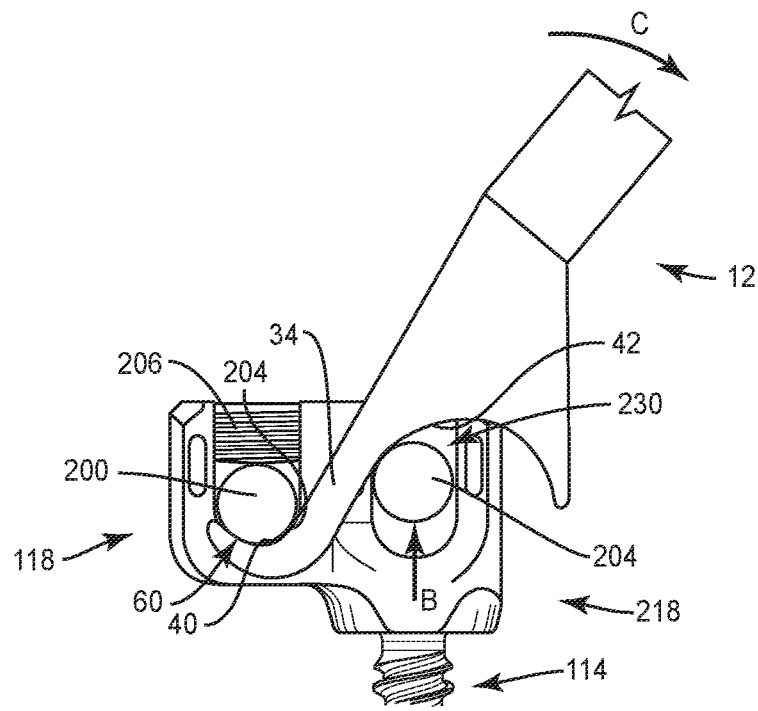
FIG. 5 is a break away side view of the components shown in FIG. 3, in a third use position.
Figure 6:
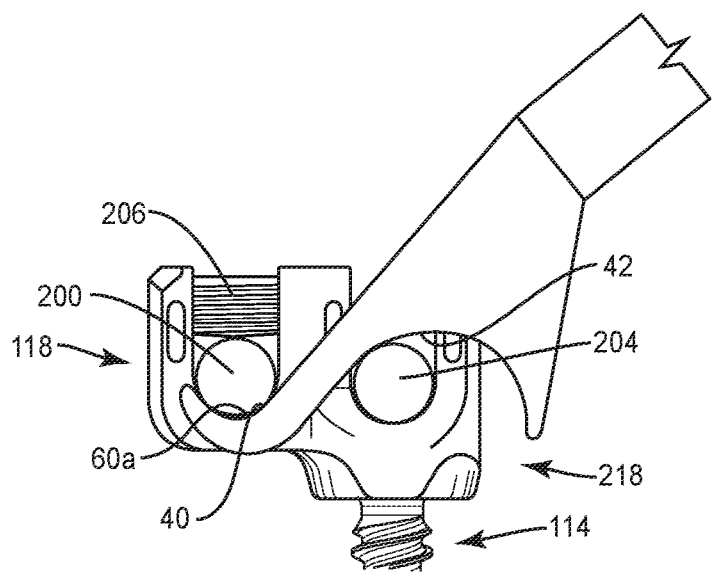
FIG. 6 is a break away side view of the components shown in FIG. 3, in a fourth use position.

Distal end 32 is rotated by manipulating handle 22 of reducer 12, in the direction shown by arrow A in FIG. 3. Reducer 12 rotates relative to axis X1 such that surfaces 40, 42 rotate relative to axis X1 and about pivot 60 in a medial-lateral orientation relative to vertebrae V. Surface 42 captures spinal rod 204 and spinal rod 204 moves along surface 42, as shown in FIG. 4. As surface 42 engages spinal rod 204, spinal rod 204 includes a resistance and/or load, in the direction shown by arrow B in FIG. 5. An effort and/or force applied to handle 22, in the direction shown by arrow C in FIG. 5, employs the mechanical advantage and leverage provided by pivot 60 to overcome the resistance and/or load of spinal rod 204, and drive and/or guide spinal rod 204 into rod slot 230. Distal end 32 is further rotated such that surface 42 reduces and/or seats spinal rod 204 with receiver 218, as shown in FIG. 6. A set screw is engaged with receiver 218 to fix spinal rod 204 with receiver 218.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In some embodiments, spinal implant system 10 can include one or a plurality of bone fasteners such as those described herein and/or fixation elements, which may be employed with a single vertebral level or a plurality of vertebral levels. In some embodiments, the bone fasteners may be engaged with vertebrae in various orientations, such as, for example, series, parallel, offset, staggered, side by side and/or alternate vertebral levels. In some embodiments, one or more of the bone fasteners described herein can include pedicle screws, uni-axial screws, sagittal adjusting screws, transverse sagittal adjusting screws, sagittal angulation screws, uni-planar screws, facet screws, fixed screws, tissue penetrating screws, expanding screws, nails and/or posts.

In some embodiments, spinal implant system 10 includes one or a plurality of alternate surgical instruments, each configured for mating engagement in a quick release configuration with spinal constructs, as described herein. In some embodiments, spinal implant system 10 includes one or a plurality of alternate surgical instruments, such as, for example, inserters, extenders, reducers, spreaders, distractors, blades, retractors, clamps, forceps, elevators and drills, which may be alternately sized and dimensioned, and arranged as a kit.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for treating a spine, the method comprising the steps of:
   connecting a bone fastener with vertebral tissue, the bone fastener including a first receiver and a second receiver;
   disposing a first spinal rod with the first receiver;
   disposing a second spinal rod adjacent the second receiver;
   engaging a first surface of a surgical instrument with the first spinal rod and a second surface of the surgical instrument with the second spinal rod, the surgical instrument including a pivot; and
   rotating the surgical instrument about the pivot to dispose the second spinal rod in the second receiver,
   wherein the surgical instrument is rotatable about the vertebral tissue in a medial-lateral orientation.

2. A method as recited in claim 1, further comprising the step of engaging a set screw with the second spinal rod and the second receiver to fix the second spinal rod with the bone fastener.

3. A method as recited in claim 1, wherein the first surface defines a first radius of curvature and the second surface defines a second radius of curvature, the first radius of curvature being greater than the second radius of curvature.

4. A method as recited in claim 1, wherein the bone fastener includes a threaded shaft aligned with the second receiver.

5. A method as recited in claim 1, further comprising fixing the first spinal rod to the first receiver with a set screw before the step of disposing the second spinal rod adjacent the second receiver.

6. A method as recited in claim 1, wherein the step of disposing the second spinal rod adjacent the second receiver comprises orienting the second spinal rod in a top loading position.

7. A method as recited in claim 1, wherein the first surface is engaged with an outer surface of the first spinal rod to define the pivot.

8. A method as recited in claim 1, wherein a portion of the first surface engages an outer surface of the first spinal rod when the first surface engages the first spinal rod, the portion of the first surface including the pivot.

9. A method as recited in claim 1, wherein engagement of the first surface with the first spinal rod creates the pivot to provide leverage.

10. A method as recited in claim 1, wherein the surgical instrument includes a lever configuration such that the pivot corresponds to engagement of the first surface and the first spinal rod to provide a fulcrum of the lever configuration.

11. A method for treating a spine, the method comprising the steps of:
providing a bone fastener, the bone fastener including a first receiver and a second receiver, the first receiver including a first inner surface, the first inner surface defining a first rod cavity, the second receiver including a second inner surface, the second inner surface defining a second rod cavity;
inserting a first rod into the first rod cavity such that an outer surface of the first rod directly engages the first inner surface;
fixing the first rod to the first receiver with a set screw;
positioning a second rod above the second rod cavity;
providing a surgical instrument comprising a body, the body extending along a longitudinal axis between opposite proximal and distal portions, the distal portion including a wall extending between opposite first and second ends;
engaging the first end with the first rod to define a pivot;
engaging the second end with the second rod; and
rotating the surgical instrument about the pivot to dispose the second rod in the second rod cavity such that an outer surface of the second rod directly engages the second inner surface.

12. A method as recited in claim 11, further comprising engaging the bone fastener with a vertebra, wherein the step of rotating the surgical instrument about the pivot comprises rotating the surgical instrument relative to the longitudinal axis such that the ends of the distal portion rotate relative to the longitudinal axis and about the pivot in a medial-lateral orientation relative to the vertebra.

13. A method as recited in claim 11, wherein the step of rotating the surgical instrument about the pivot comprises capturing the second rod with a surface of the second end such that the second rod moves along the second inner surface to create a load in an upward direction relative to the second rod cavity.

14. A method as recited in claim 13, wherein applying a force to a handle of the surgical instrument rotates the surgical instrument about the pivot such that leverage provided by the pivot overcomes the load and drives the second rod in a downward direction relative to the second rod cavity to engage the outer surface of the second rod with the second inner surface.

15. A method for treating spine, the method comprising the steps of:
connecting a bone fastener with vertebral tissue, the bone fastener including a first receiver and a second receiver;
disposing a first spinal rod with the first receiver;
disposing a second spinal rod adjacent the second receiver;
engaging a first surface of a surgical instrument with the first spinal rod and a second surface of the surgical instrument with the second spinal rod, the surgical instrument including a pivot; and
rotating the surgical instrument about the pivot to dispose the second spinal rod in the second receiver,
wherein the first surface is engaged with an outer surface of the first spinal rod to define the pivot.

16. A method as recited in claim 15, further comprising fixing the first spinal rod to the first receiver with a set screw before the step of disposing the second spinal rod adjacent the second receiver.

17. A method as recited in claim 15, wherein the step of disposing the second spinal rod adjacent the second receiver comprises orienting the second spinal rod in a top loading position.

18. A method as recited in claim 15, wherein the first surface defines a first radius of curvature and the second surface defines a second radius of curvature, the first radius of curvature being greater than the second radius of curvature.

19. A method as recited in claim 15, wherein the bone fastener includes a threaded shaft aligned with the second receiver.

20. A method as recited in claim 15, wherein the second spinal rod directly engages the second receiver.

* * * * *